United States Patent
Schultz

(10) Patent No.: US 12,427,194 B2
(45) Date of Patent: Sep. 30, 2025

(54) COMPOSITION AND METHODS FOR TREATING ACUTE DIARRHEA AND ENTERIC

(71) Applicant: Anubis Bio Corporation, San Francisco, CA (US)

(72) Inventor: Thomas A. Schultz, Oviedo, FL (US)

(73) Assignee: MAMMAL LABS INC., San Jose, CA (US)

( * ) Notice: Subject to any disclaimer, the term of this patent is extended or adjusted under 35 U.S.C. 154(b) by 0 days.

(21) Appl. No.: 17/202,007

(22) Filed: Mar. 15, 2021

(65) Prior Publication Data

US 2021/0196825 A1    Jul. 1, 2021

Related U.S. Application Data

(62) Division of application No. 16/591,025, filed on Oct. 2, 2019, now Pat. No. 10,973,918.

(60) Provisional application No. 62/740,769, filed on Oct. 3, 2018.

(51) Int. Cl.
| | |
|---|---|
| *A61K 39/42* | (2006.01) |
| *A23K 20/147* | (2016.01) |
| *A23K 50/40* | (2016.01) |
| *A61K 35/20* | (2006.01) |
| *A61K 35/57* | (2015.01) |
| *A61P 1/12* | (2006.01) |
| *A61P 31/04* | (2006.01) |
| *A61P 31/20* | (2006.01) |
| *A61K 39/00* | (2006.01) |

(52) U.S. Cl.
CPC ............ *A61K 39/42* (2013.01); *A23K 20/147* (2016.05); *A23K 50/40* (2016.05); *A61K 35/20* (2013.01); *A61K 35/57* (2013.01); *A61P 1/12* (2018.01); *A61P 31/04* (2018.01); *A61P 31/20* (2018.01); *A61K 2039/552* (2013.01)

(58) Field of Classification Search
None
See application file for complete search history.

(56) References Cited

FOREIGN PATENT DOCUMENTS

| WO | WO-2012071346 A1 * | 5/2012 | ............. A61K 35/20 |
|---|---|---|---|
| WO | WO-2015004181 A1 * | 1/2015 | ............. A61K 39/00 |

OTHER PUBLICATIONS

Ian Battersby and Andrea Harvey, Differential diagnosis and treatment of acute diarrhoea in the dog and cat, in Practice, Sep. 2006, pp. 480-488.

\* cited by examiner

*Primary Examiner* — Oluwatosin A Ogunbiyi
(74) *Attorney, Agent, or Firm* — David R. Stevens; Stevens Law Group

(57) ABSTRACT

The composition may be used therapeutically or prophylactically and is directed toward a cluster of diarrhea-causing pathogens which cause illness or death in animals, including dogs and cats. It is prepared from a powdered egg preparation and powdered protein matrix, such as bovine colostrum. The eggs are collected from hens which have been immunized with the relevant pathogens or toxins. When the matrix includes colostrum, the powdered colostrum is derived from non-hyperimmune cattle. The vaccination strategy includes the use of antibody cross-reactivity between toxins or pathogens which cause diarrhea. For some diseases, including canine parvo, the clinical improvement using this therapeutic exceeds the standard of care. Instead of a pharmaceutical product, this composition is an orally administered food product with the same safety profile as eggs and milk.

18 Claims, 3 Drawing Sheets

COMPOSITION AND METHODS FOR TREATING ACUTE DIARRHEA AND ENTERIC

CROSS REFERENCE TO RELATED APPLICATIONS

This application is a divisional of U.S. Pat. No. 10,973,918 filed on Oct. 2, 2019, which in turn claims the benefit of U.S. Provisional Patent Application Ser. No. 62/740,769 filed on Oct. 3, 2018, which is hereby incorporated by reference in its entirety.

FIELD OF INVENTION

The invention provides compositions and methods for treatment of diarrhea and enteric infections in animals including dogs and cats. The treatment comprises a food substance which provides passive immunity against pathogens.

BACKGROUND OF THE DISCLOSURE

Antibodies, both naturally occurring and their synthetic analogues, are known therapeutic agents in animals. Antibodies bind a portion of the antigen (the antigenic determinant or epitope) with the antigen combining site on the antibody. Antibodies are capable of high degrees of specificity enabling targeted application to specific pathogens. However, this high specificity can lead to excessively limited binding attributes, where agents or antigens that are functionally identical (for example, cause the same disease or symptoms) do not react identically with the immunoreagent or immunotherapeutic. Cross-reactivity on the other hand is the reaction between an antigen and an antibody that was generated against a similar but different antigen. Controlled cross-reactivity may constructively be used to broaden the binding range of the antibody, enabling broad spectrum protection against pathogens other than those specifically targeted.

In mammalian species, immunity to pathogens is transferred from mother to offspring via maternal antibodies provided by the placenta or colostrum. The mother is able to transfer only those antibodies that were built up by her body due to natural exposure or vaccinations. However, her level of transfer of antibodies is influenced by how recently exposure to specific pathogens occurred. If the maternal colostrum contains an insufficient quantity of antibodies specific for certain pathogens, the neonate will have a deficient level of immunity for those diseases.

Colostrum has evolved naturally in mammals specifically to deliver its components to neonates into and through the gastrointestinal tract in a very concentrated low-volume form. Colostrum is known to contain antibodies including IgA, IgG, and IgM. Other components of colostrum include lactoferrin, lysozyme, lactoperoxidase, complement, and proline-rich polypeptides (PRP). Other components in colostrum have been shown to protect and support the antibody activity in the gastrointestinal tract.

The antibodies and cofactors in colostrum can provide a passive immunity to the recipient. Normally, antibodies and cofactors are passed to the neonate from the mother and provide the first protection against pathogens. Growth factors in colostrum also stimulate the development and repair of the gut. Other components in colostrum help protect maternal antibodies on their journey through the digestive system and support antibody activity in the intestine. This is a particularly important function in bovine species which have a more extensive gastrointestinal tract than many other mammals.

Colostrum is naturally designed to serve as a protective/reactive matrix within a gastrointestinal environment. It helps to regulate the intestinal environment, rendering it hostile to foreign pathogens. As an example, colostrum contains lactoferrin, an iron-binding protein that prevents bacteria and viruses from obtaining iron necessary for replication. Colostrum also selectively fertilizes certain probiotic species that, in turn, help to ward off infection. Colostrum is a source of two major growth factors, Transforming Growth Factors (TGF) alpha and beta, as well as a source of Insulin-Growth Factors 1 and 2. These factors promote tissue repair and development. Colostrum is also a source of Hepatocyte Growth Factor (HGF, also known as "scatter factor"), which stimulates the growth and expansion of intestinal wall cells.

Specific antibody production via immunization of an avian species, for example, chickens, is well documented. When immunized with an appropriate antigen, the hen responds by producing IgY antibodies which are concentrated in the egg yolk for use by the chick during the first weeks of life. Transfer of IgY antibodies from the yolk to the developing chick substitutes for the mammal delivering antibodies to the neonate in the form of colostrum.

IgY antibodies from avian eggs have been shown to be effective against pathogens residing in the gastrointestinal tract of mammals. Unfortunately, orally delivered antibody therapeutic effectiveness is diminished by passage through the stomach and exposure to gastric acid and digestion enzymes.

Attempts have been made to deliver therapeutic antibodies to treat human gastrointestinal infections by providing either bovine colostrum or avian antibodies individually. These attempts resulted in poor or inconsistent clinical outcomes. However, the combination of avian-produced antibodies using bovine colostrum as a protective/reactive matrix has been demonstrated to be a reliably effective therapy for diarrhea and enteric infections in humans.

Members of the Canidae and Felidae families share many characteristics with humans and bovine species. In particular, they utilize maternal passive immunity to protect neonates, are subject to infectious diarrhea and other enteric diseases, and suffer from a lack of effective treatment for common diarrhea infections. The standard of care for dog or cat diarrhea is fasting or a bland diet and a course of antibiotics, even if the pathogen is a virus.

For some infections, this is can be deadly. For example, canine parvovirus is a highly contagious viral disease that can produce a life-threatening illness. The virus attacks rapidly dividing cells in a dog's body, most severely affecting the intestinal tract. Parvovirus also attacks the white blood cells, and when young animals are infected, the virus can damage the heart muscle and cause lifelong cardiac problems. Parvovirus is a widespread canine infection that attacks young and unvaccinated dogs.

There are no drugs or treatments generally available that can kill parvovirus. Treatment consists of aggressive supportive care to control symptoms. Dogs infected with parvovirus need intensive treatment in a veterinary hospital, where they receive antibiotics (which has no effect on the parvovirus), drugs to control the vomiting, intravenous fluids, and other supportive therapies. This entails considerable expense; the average hospital stay is about 5-7 days.

Even with medical support, canine parvo mortality rates range from 20%-50%, depending upon the level of palliative care.

There are currently 90 million dogs and 80 million cats in the U.S., each averaging 2 to 3 diarrhea episodes per year. Approximately 20% of 220 million veterinarian visits in the U.S. are related to canine or feline diarrhea. There is currently no "first line" treatment available that provides timely relief of diarrhea sequalae and neutralization of the underlying infection at a nominal cost.

BRIEF SUMMARY OF THE INVENTION

We disclose a composition and method of its use for treatment of pathogen-induced diarrhea in animals including, but not limited to, members of the Canidae or Felidae families. The composition includes targeted avian-sourced antibodies mixed with a protective protein matrix to introduce effective passive immunity to an animal in need thereof. The targeted antibodies are embedded in the protective protein matrix so as to be reactive with specific pathogens, toxins, or other targets related to the disease state while being protected from destruction by the gastrointestinal environment. The antibodies are a mixture of IgY antibodies and include antibodies which are specific to multiple antigens which are derived from multiple epitopes associated with diarrhea-causing disease. These epitopes may be organisms, toxins, or a mixture of organisms and toxins, each of which cause diarrhea in animals.

The protective protein matrix may be derived from a non-hyperimmune animal source. In some embodiments, this matrix includes colostrum from a non-hyperimmune animal. The non-hyperimmune animal may be a ruminant, for example, a lactating cow. In other embodiments, the protein source may be derived from another bodily fluid or tissue obtained from a non-hyperimmune animal. In some embodiments, the protective protein matrix may make up 20% or more of the composition.

The antibodies may be produced by vaccinating a bird, for example, a chicken, with antigens found in diarrhea-causing organisms or toxins produced by these organisms. Eggs laid by the birds contain IgY antibodies which interact with the organisms or toxins. Cross-reactivity of antibodies is used to create a mixture of antibodies which adhere to clusters of antigens found in different organisms or toxins all of which cause diarrhea in animals. Cross-reactive antibodies may be produced by vaccinating the birds with antigens which are common to groups of diarrhea-causing organisms or toxins. Consequently, the antibodies in the disclosed therapeutic may be used to treat or prevent diarrhea caused by a broader range of organisms including diarrhea in animals in which the class of organism causing the disease is known but not the specific organism within the class.

Examples of diarrhea-causing organisms from which the antigens used to produce the antibodies included in the composition include the following: a species of the genus *Clostridium*, a species of the genus *Yersinia*, a species of the genus *Brachyspira*, a species of the genus *Campylobacter*, *Escherichia coli*, *Helicobacter* spp., a species of the genus *Salmonella*, a species of the genus *Leptospira*, *Providencia alcalifaciens*, *Mycobacterium paratuberculosis*, *Lawsonia intracellularis*, bovine viral diarrhea virus, infectious bovine rhinotracheitis virus, coronavirus, rotavirus, parvovirus, paramyxovirus, hepatitis virus, feline leukemia virus, feline immunodeficiency virus, feline panleukopenia virus, astrovirus, transmissible gastroenteritis, African swine fever virus (genotypes I-XXIII), *Giardia*, *Coccidia*, *Entamoeba histolytica*, *Cryptosporidium*, roundworm, whipworm, spirochetes, yeasts, and molds.

BRIEF DESCRIPTION OF THE DRAWINGS

In order that the advantages of the invention will be readily understood, a more particular description of the invention briefly described above will be rendered by reference to specific embodiments illustrated in the appended drawing. Understanding that this drawing depicts only a typical embodiment of the invention and is not therefore to be considered limiting of its scope, the invention will be described and explained with additional specificity and detail through use of the accompanying drawing.

DETAILED DESCRIPTION OF THE DISCLOSURE

Definitions

Figure 1:
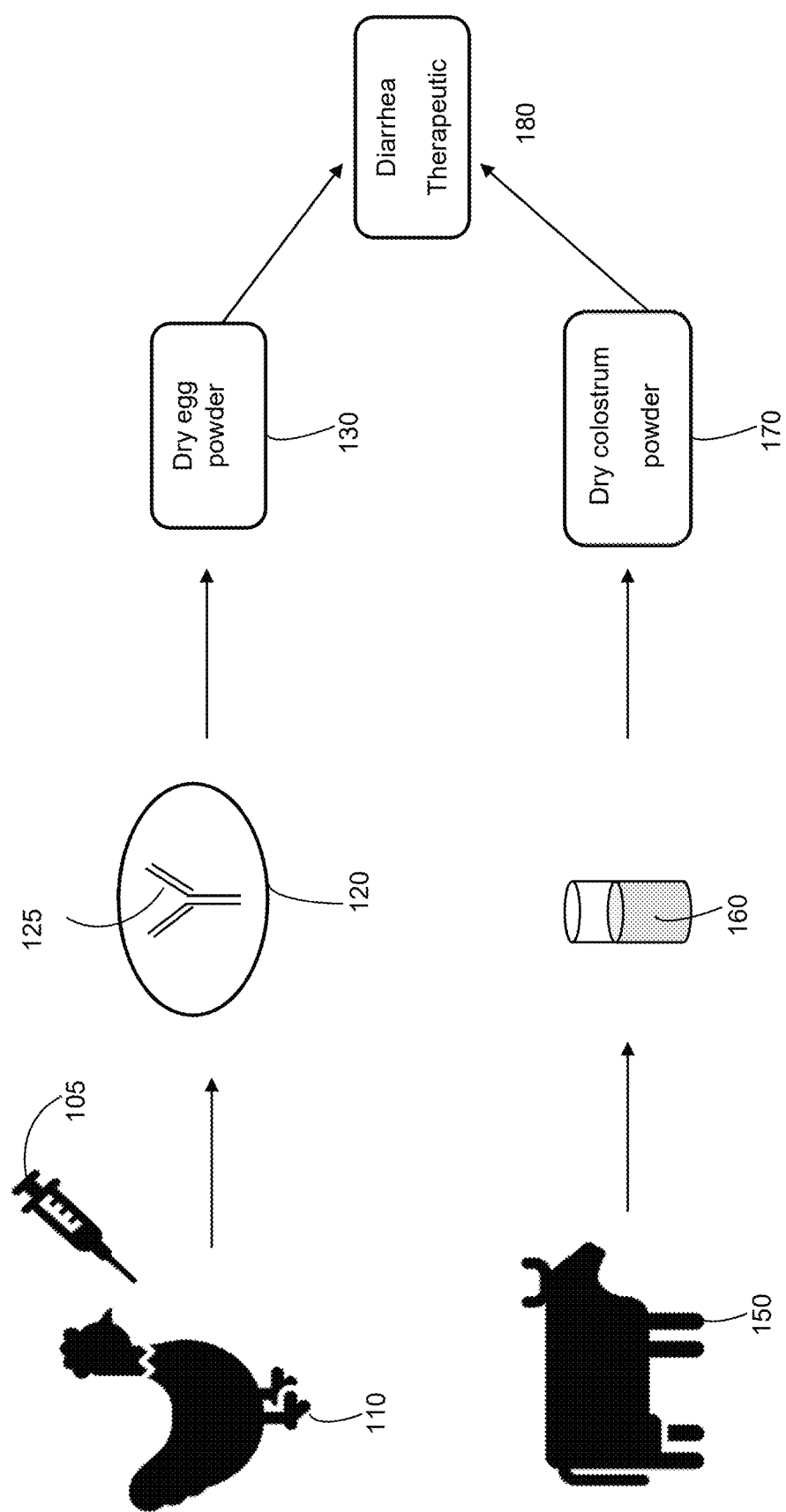
FIG. 1 is a schematic drawing of a method of producing the disclosed composition.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "organism" means a form which may have a single cell or multiple cells, and which include bacteria, viruses, and parasites.

As used herein, "pathogen" means an organism which causes disease or untoward effects in a host and which include bacteria, viruses, and parasites.

While this invention is susceptible of embodiment in many different forms, there is shown in the drawings, which will herein be described in detail, specific embodiments with the understanding that the present disclosure is to be considered as an exemplification of the principals of the invention and is not intended to limit the invention to the illustrated embodiments.

We disclose a therapeutic composition for use in the prevention or treatment of pathogen-induced diarrhea in animals, including dogs or cats. Methods of production of the therapeutic composition and methods of treating an animal, including a dog or a cat, to prevent or treat pathogen-induced diarrhea are also disclosed.

There is a clear need for low cost and effective treatments for many animal gastrointestinal pathogens, and orally administered antibodies are candidates for this role. In addition to demonstrated efficacy, orally administered antibodies are typically non-immunogenic so do not result in an adverse immunological response in the animal receiving the composition. They are typically well tolerated with no adverse side effects reported and comparatively no different reactions than a comparable ingested food product. Notably several products containing orally administered antibody have received GRAS (Generally Recognized as Safe) certification by the U.S. Food and Drug Administration.

The disclosed composition includes IgY antibodies may be derived from eggs laid by chickens or other avian species (egg-laying hens). These hens have been immunized against one or more pathogens which cause diarrhea in dogs, cats, or other animals. In the example in which chickens are used to produce the eggs, the chickens may be any domestic bird of the subspecies *Gallus gallus domesticus*. Examples include, but are not limited to, the following breeds of *Gallus domesticus*: Rhode Island Red, Leghorn, Australorp, Lohmann Brown Classic, Sussex, Golden Comet, Marans, Plymouth Rock, Barnevelder, Buff Orpington, Ameraucana, La Brese, and Hamburg. These examples are breeds of chickens which are known to be prolific egg producers. However, other breeds of chicken and other avian species are within the scope of this disclosure. In some embodiments, the chickens may comprise breeds meeting safety and process regulations for animal consumption as promulgated by relevant government authority (for example, the United States Department of Agriculture ("USDA")).

Prior to egg collection, the hens may be immunized with a vaccine comprising at least one antigen which initiates production of antibodies directed against one or more diarrhea-causing pathogens. The vaccine may be produced by any method known in the art. Examples include attenuated live vaccines, modified live vaccines, chemically altered vaccines, killed vaccines, toxoid vaccines, DNA vaccines, subunit vaccines, recombinant vaccines, polysaccharide vaccines, and conjugate vaccines. The vaccines may be directed against viruses, bacterial pathogens, parasites, yeasts, or molds. The vaccines may also be directed against adhesins or toxins produced by pathogens. In some embodiments, the vaccines may include one or more adjuvants which enhance the immunogenicity of the vaccine.

In some embodiments, the hens may be immunized with vaccines which include a live, wild-type pathogen. Vaccines are typically created using pathogens which have been rendered less virulent (by modifying or killing it) and unlikely to result in clinical illness in the organism receiving the vaccine. However, a pathogen that causes diarrhea in an animal may not cause any illness in an avian species although the bird may produce antibodies against it. Consequently, the hens remain healthy but are still able to raise antibodies against the vaccine components which bind to the pathogens within an infected dog, cat, or other animal. An advantage to using live, wild type pathogens in vaccines is that they are more immunogenic than their attenuated counterparts resulting in greater antibody production. Accordingly, adjuvants may not be required in these vaccines.

Diarrhea-causing pathogens against which the hens may be immunized include *Clostridium perfringens* and other Clostridial species, *Campylobacter*, *Escherichia coli* (including enterotoxigenic (ETEC)), *Helicobacter* spp., species of the genus *Salmonella* including *Salmonella* spp., *Salmonella typhimurium*, and *Salmonella choleraesuis*, species of the genus *Leptospira, Providencia alcalifaciens*, species of the genus *Yersinia* including *Yersinia pseudotuberculosis* and *Yersinia enterocolitica*, *Mycobacterium paratuberculosis, Brachyspira pilosicoli*, atypical *Brachyspira, Brachyspira hyodysenteriae, Lawsonia intracellularis,* bovine viral diarrhea (BVD) virus, infectious bovine rhinotracheitis (IBR) virus, coronavirus, rotavirus, parvovirus, paramyxovirus, hepatitis virus, feline leukemia virus, feline immunodeficiency virus, feline panleukopenia virus, astrovirus, transmissible gastroenteritis (TGE) virus, African swine fever virus (genotypes I-XXIII), parasites (e.g., *Giardia, Coccidia, Entamoeba histolytica*, species of the genus *Cryptosporidium* including *Cryptosporidium parvum*, roundworm, whipworm, *Aeromonas hydrophilia*, spirochetes including *trichomonas*), yeasts, molds, and other diarrhea causing pathogens.

In some embodiments, each hen may be immunized with a single diarrhea-causing pathogen. In this example, multiple hens may each be immunized with a different single diarrhea-causing antigen and the eggs from each hen may be combined to result in a product which includes IgY antibodies against different antigens. In other embodiments, a single hen may be immunized with two or more diarrhea-causing pathogens resulting in IgY antibodies against the different antibodies being present in the same egg.

An example of method of selecting groups of pathogens against which a hen may be vaccinated is based on known multiple causative organisms in diarrhea. These causative organisms can be organized into common clusters of structurally related toxins or diarrhea causing subunits or the organism, to which a series of broad-spectrum neutralizing antibodies can be created. When admixed into a formulation with clinically effective titers, these antibodies can be used as a broad-spectrum organism-independent therapeutic intervention for toxin-mediated diarrhea.

By using this method of selecting pathogens for vaccination, it may not be necessary to know the precise pathogen which is causing diarrhea in the animal to receive the composition. Also, when used prophylactically, the animal is protected against many diarrhea-causing organisms. For example, the antibodies raised in the hens may use a controlled form of cross-reactivity to multiple clusters of related target antigens. There exists a degree of structural similarity in related clusters of target antigens, without regard to the organism or toxin that is the source of the antigen. By raising antibodies against antigens common to these related clusters, a broad-spectrum therapeutic intervention is created for use in situations where the class of causative agent, but not the precise or specific causative agent is known or suspected, or under circumstances where multiple (mixed) causative agents are active.

Furthermore, the disclosed invention provides a path for an effective and immediate response to an emergent undifferentiated pathogen strain with a new combination of features, some of which already reside in other microbes. For example, new combinations of pathogen features result from random mutation, inclusion of DNA from other microbes, or antibiotic-mediated selective evolution. These events create new, highly virulent pathogen strains with limited response to existing medical treatments. These altered strains often result in high morbidity/mortality for months or years until a vaccine or other treatment is developed. An example is the African swine fever virus which has 23 genotypic variations. The strategy for preparing a vaccine as described herein could address all current and future variations of the African swine fever virus.

This approach takes advantage of both the specificity and cross-reactive attributes of the antibodies. In this embodiment, antibodies are designed to bind to several closely related epitopes that are present within a structurally related cluster of antigens. These antigens may differ markedly in other respects, and may originate from diverse sources, organisms, or species but have the common effect of causing diarrhea in animals including cats and dogs.

In this case the inoculant or immunogen is selected to a common or preserved component or region of the targeted antigen cluster, while ignoring the variable or distinguishing components or regions of the individual members of the cluster of related antigens. The method involves the preparation a vaccine which will be administered to the birds and which comprises an appropriate immunogen with characteristics that elicit the production of antibodies that are cross-reactive to desired instances of that epitope, but which are not reactive to other epitopes.

One example of this embodiment includes the production of antitoxin antibodies that are specifically reactive to clusters of structurally related toxins. These example antibodies would have effect without regard to the species originating the toxin. For example, the antibodies raised against the structurally related toxins may be neutralizing antibodies, capable of neutralizing or inactivating the biological activity of the target toxins.

Such a broad-spectrum neutralizing antibody could be used as disclosed herein to intervene in certain types of diarrhea where the toxin mediating the symptoms is one of a cluster of toxins without requiring knowledge of which organism was causative. Further, if a therapeutic according to the instant disclosure was prepared containing multiple antibodies in clinically effective amounts, the formulation could be used to intervene in cases where the active toxin responded to any of the antibodies in the admixture.

This method can be extended to include any number of toxin clusters, and to include broad-spectrum neutralizing antibodies against mediators of other toxin-like reactions (for example viral toxin-like phenomena), to create a broadly applicable intervention to diarrhea. Using these antibodies to prepare a therapeutic as disclosed herein, symptoms and pathology may be managed or prevented without knowledge of the infectious causes, or in cases where there are multiple infectious causes.

Protocols for immunizing the hens with the vaccine may be according to those known in the art for initiating antibody production in chickens. In an example, the hens may receive two or more vaccinations at least two weeks apart. In some embodiments, the vaccinations may begin when the hens are 18 weeks of age or older. Booster vaccines may be given to the hens 6 months after the first vaccination.

In some embodiments, the vaccines are administered to the hens subcutaneously. In other embodiments, the vaccines are administered through intramuscular, oral, intravenous, buccal, nasal, or dermal procedures.

After the immunization process, whole shell eggs may be collected from the hens. The yolks of these eggs contain concentrated IgY which bind to the one or more pathogens against which the laying chicken was vaccinated. In other embodiments, the yolk of the eggs may be isolated from the egg whites.

A dehydrated egg powder may be produced from the eggs (either whole shell or isolated yolks) according to procedures known in the art. In one embodiment, the eggs may be pan dried using commercial dehydrators suitable for liquid egg. In some embodiments the commercial dehydrators may meet food processing standards as promulgated by relevant regulatory bodies (for example, USDA). The drying temperature may be at least 138 F, but not to more than 150 F which is sufficient to pasteurize egg and dry to powder within 15 hours. The dehydrated egg product may then be ground produce a powder suitable for mixing.

In another embodiment, the eggs pay be spray dried. In this embodiment, the liquid eggs may be pasteurized at 140 F immediately prior to spray dry using dedicated food quality process equipment following relevant regulatory guidelines. The dried egg product may then be ground produce a powder suitable for mixing.

Additionally, other drying processes, lyophilization, pasteurization, and preservation methods may be used to process the eggs. Furthermore, the antibodies in the eggs may be concentrated, separated, or purified in various ways known in the art. The antibodies produced as disclosed herein may be purified, treated, or retained in the egg material for use in manufacturing the disclosed therapeutic.

The egg powder preparation may be embedded in a within a protective protein matrix, for example colostrum, for oral administration. In some embodiments, the colostrum may be bovine colostrum. In some embodiments, the colostrum may be collected from non-hyperimmune ruminants. In some embodiments, non-hyperimmune ruminants may be non-hyperimmune cattle. In some embodiments, the colostrum may comprise of whole colostrum. The colostrum may be dehydrated and ground to a powder using techniques known in the art. Methods described herein for dehydrating the egg preparation may also be used to prepare colostrum powder.

Colostrum serves to provide additional protective and efficacious attributes to the antibody preparation. Any combination of antibodies may be used within a colostrum matrix, including but not limited to a combination of anti-pathogen, anti-toxin, and anti-adhesin antibodies.

In addition to colostrum, other protein sources may be used as a protective matrix and mixed with the egg powder preparation. While colostrum includes antibodies derived from the lactating animal, its purpose in this composition is to act as a carrier and to protect the IgY antibodies derived from the egg powder preparation. Examples of other protein sources for use in preparing the protective protein matrix include serum albumin, for example, bovine serum albumin. Dehydrated egg whites may also be used as a protein matrix. While liquid egg whites as found in a chicken egg have approximately 10% protein, a more concentrated protein mixture may be created by dehydrating the egg whites to produce a powder that is added to the egg powder preparation. Protein powder derived from other animal tissues, for example, muscle, gelatin, or collagen of non-hyperimmune animals may also be dehydrated and used to create a powdered protein matrix. Yeast, whey, or whole milk are additional examples of protein sources which may be dehydrated to create a powdered protein matrix.

Once the preparation of dried egg material including antibodies and the dried colostrum are prepared, the two may be mixed to create a powdered substance for using in treating animals with diarrhea. The protective protein powder may be provided in proportions of between 20% to 80% by weight of the egg and protein mixture. The powdered egg mixture may be provided in proportions of between 80% and 20% by weight of the egg and protein mixture. In some embodiments, the mixture contains approximately 55% protein powder and approximately 45% powdered egg preparation by weight. In some embodiments the mixture contains approximately 45% protein powder and approximately 55% powdered egg preparation by weight. In some embodiments, the mixture contains approximately 50% protein powder and approximately 50% powdered egg preparation by weight.

Figure 2:
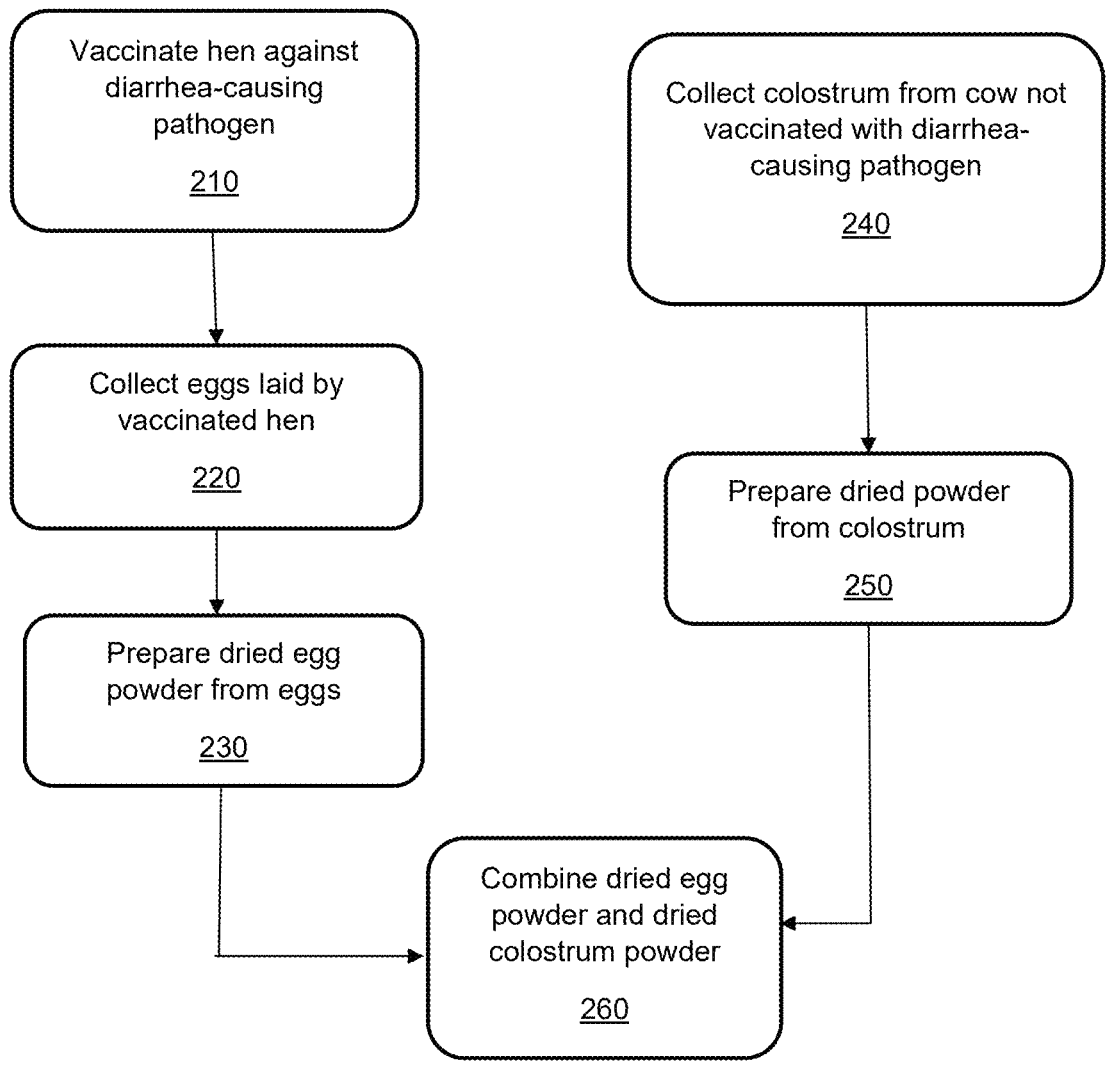
FIG. 2 is a flow chart describing a method of producing the disclosed composition.

FIGS. 1 and 2 describe embodiments of the preparation of the egg powder and protective protein powder mixture. In FIG. 1, chicken 110 is receiving vaccine 105 which includes multiple antigens associated with diarrhea-causing pathogens or toxins. Chicken 110 then lays egg 120 which includes antibodies, including antibody 125 inside it. Many antibodies are present in egg 120 although only antibody 125 is depicted for purposes of clarity. Egg 120 is converted to a dry egg powder using techniques described herein. In this embodiment, the protective protein matrix is prepared from non-hyperimmune bovine colostrum. Lactating cow 150 is a non-hyperimmune animal from which colostrum 160 is collected. Colostrum 160 is converted to a dry colostrum powder 170 using techniques described herein. Dry egg powder 130 and dry colostrum powder 170 are combined in ratios disclosed herein to produce diarrhea therapeutic 180.

FIG. 2 is a flow chart which describes the process depicted in FIG. 1. In step 210, the hens, are vaccinated against one or more diarrhea-causing pathogen or toxin. After a sufficient time to raise antibodies in response to the vaccine, the hens lay eggs which are collected in step 220. The eggs contain antibodies against the epitopes in the vaccine. In step 230, dried egg powder is prepared from the eggs. In this embodiment, colostrum is used as the protective protein matrix. In step 240, colostrum from a non-hyperimmune cow is collected. Specifically, the cow has not been vaccinated against diarrhea-causing pathogens or toxins. The cow is milked to collect colostrum and a dried powder is prepared from the colostrum using techniques described herein (step 250). In step 260, dried egg powder from step 230 is combined with dried colostrum powder from step 250 in ratios disclosed herein to produce the therapeutic composition.

The egg and colostrum (or other matrix protein) mixture may be provided in powdered form. Alternatively, the egg and colostrum mixture may be processed to produce tablets, chewable pills, syrups, elixirs, or aqueous suspensions. Any form known in the art which may be administered orally to an animal is within the scope of this disclosure. Other additives, including preservatives or flavorings, may be included in the final mixture.

One or more of electrolytes, vitamins, and one or more probiotic cultures may also be included in the therapeutic to further support treatment of diarrhea. Probiotics are microbes that are normally found in the gut. They may be bacteria or yeast. When present in proper amounts, probiotic microbes aid in digestion, inhibit growth of pathogenic organisms, and synthesize nutrients. They may also support the host's immune system or have anti-inflammatory activity. In fact, different probiotic strains provide different benefits to the host. It is for at least this reason that probiotic supplements are often provided as a mixture of multiple strains. The mixture may include a plurality of bacteria strains, a plurality of yeast strains, or a plurality of both bacteria and yeast strains. In their absence or in reduced amounts, pathogenic microbes may proliferate in the gut creating an opportunistic infection. Severe diarrhea is one instance in which the normal gut probiotic microbes are reduced creating an environment for pathogenic organisms to multiply.

Probiotic supplements administered orally have shown inconsistent efficacy in treating gastrointestinal disease in dogs. Part of the reason is thought to be that, like the antibodies discussed herein, the probiotic microbes do not survive the acid environment of the upper gastrointestinal tract. Consequently, the protection the colostrum or other protein matrix provides to the antibodies in the disclosed therapy may also protect the probiotic microbes. Therefore, a reduced number of colony forming units (CFUs) in each dose of the disclosed therapy may provide the desired efficacy relative to providing probiotic cultures alone. Furthermore, the probiotics may add to the therapeutic effect of the antibodies in the disclosed therapy.

In some embodiments, the microbial strains which may be included as probiotics include one or more of the following list: *Enterococcus faecium* (including, but not limited to strain SF68), *Lactobacillus acidophilus, Lactobacillus casei, Lactobacillus plantarum, Bifidobacterium bifidum*, VSL #3, *Lactobacillus rhamnosus* (including, but not limited to strain GG (LGG)), *Bifidobacterium animalis* (including, but not limited to, strain AHC7). The latter is reported to be especially effective to combat *Clostridium difficile* infections of the gut. Other strains known in the art may also be included in the disclosed therapy.

In addition to probiotics, some embodiments may include prebiotics which provide nutrients for the probiotic microbes. The protein matrix may act as a prebiotic. Other prebiotics which may be included are fructooligosaccharides (FOS), beet pulp, raw garlic, dandelion greens, wheat dextrin, chicory, fermented vegetables, and other prebiotics known in the art.

The therapeutic may be provided to a cat, dog, or other animal in doses that may depend on the animal's body weight, the severity of the disease, and whether the therapeutic is being used prophylactically or to treat existing illness. In an example, a single dose may comprise 3-10 grams of the powdered egg and protein matrix mixture, excluding other additives which may be present in the final product. In some embodiments, a single dose may comprise approximately 5 grams of the powdered egg and protein matrix mixture, excluding other additives which may be present in the final product. The therapeutic may be administered by sprinkling the dry product onto food which the animal may then ingest. The therapeutic in dry form may be mixed with water or other ingestible liquid and mixed into or decanted onto food which the animal may then ingest. The therapeutic in dry form may be mixed with water or other ingestible liquid and administered into the animal's mouth using a syringe or provided for the animal to drink or administered directly into the animal's stomach through a nasogastric tube. In summary, any method of administering the product into the gastrointestinal tract of the animal to be treated is within the scope of this disclosure.

Figure 3:
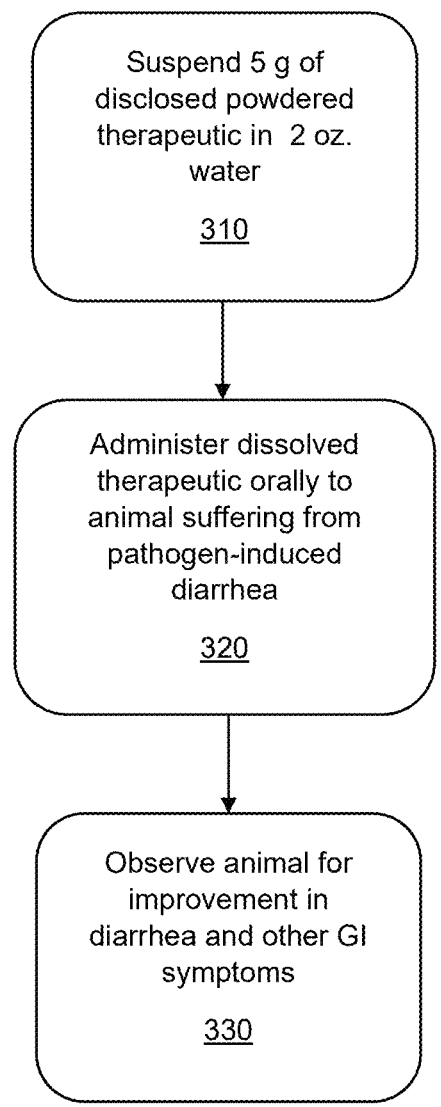
FIG. 3 is a flow chart describing a method of treating a subject using the disclosed composition.

FIG. 3 summarizes an embodiment in which an animal suffering from diarrhea is treated with the disclosed composition. In step 310, a user suspends 5 g of the powdered therapeutic as described herein in 2 ounces of water. The suspended therapeutic is administered orally to an animal suffering from diarrhea caused by a pathogen or toxin (step 320). The animal is then observed for improvement in diarrhea, vomiting, or other gastrointestinal symptoms (step 330).

While the Examples below illustrate the disclosed composition and embodiments of its method of use in dogs, use of the composition in cats, cattle, horses, swine, sheep, goats, camels, rabbits, guinea pigs, chinchillas, and other animals is within the scope of this disclosure. In some embodiments, the animals may be non-neonate animals.

In an example, calves from bovine species often suffer from diarrhea caused by one or more of a variety of infectious pathogens. Calf scours represents a significant loss to cow-calf producers. Examples of infectious pathogens which may cause calf scours include *E. coli, Salmonella* spp., *Clostridium perfringens*, rotavirus, corona virus, bovine viral diarrhea (BVD) virus, infectious bovine rhinotracheitis (IBR) virus, cryptosporidium, Coccidia, yeasts, and molds.

Similarly, the young offspring of equine species often suffer from pathogen-induced diarrhea. These pathogens including *C. perfringens, C. difficile, Salmonella* spp., *E. coli, Cryptosporidium parvum*, rotavirus, coronavirus, and *Aeromonas hydrophilia*.

Swine are also prone to diarrhea cause by pathogens. Examples of pathogens which may cause diarrhea in swine include *Brachyspira pilosicoli*, atypical *Brachyspira, Brachyspira hyodysenteriae, Lawsonia intracellularis, Salmonella* spp., *Salmonella typhimurium, Salmonella choleraesuis, Yersinia pseudotuberculosis, Escherichia coli, Clostridium perfringens, Cryptosporidium* spp., *Giardia* spp., transmissible gastroenteritis (TGE) virus, African swine fever virus (genotypes I-XXIII), and whipworm.

Sheep and goats are known to suffer from diarrhea-causing illnesses as a result of pathogens. These pathogens include *Ccoccidia*, species of the genus *Yersinia* (including *Yersinia pseudotuberculosis* and *Yersinia enterocolitica*), species of the genus *Salmonella, Escherichia coli, Cryptosporidium* spp., *Clostridium perfringens, Mycobacterium paratuberculosis*, rotavirus, and coronavirus. Worms (GI helminths) are also a common cause of diarrhea in sheep and goats.

The disclosed composition and methods of use may be applied to the livestock species discussed above and others suffering from diarrhea. In some embodiments, the animals may be non-neonate animals. The composition may include antibodies which adhere to the diarrhea-causing organisms which cause diarrhea in these species as discussed herein. These antibodies may be raised in avian eggs as disclosed herein.

In addition to treating or preventing diarrhea, the disclosed inventive step may be used to produce compositions which treat or prevent other gastrointestinal diseases and symptoms including colitis, constipation, bloating, gastritis, gastrointestinal ulcers, hemorrhagic gastritis, inflammatory bowel disease, and malabsorption. Rather than targeting diarrhea-causing organisms and toxins, the antibodies will be created to adhere to organisms and toxins which cause one of the listed gastrointestinal diseases or symptoms.

In some subjects, the gastrointestinal discomfort may be the result of an imbalance in the subject's gastrointestinal biome. Opportunistic microbial organisms may take over the gastrointestinal biome at the expense of other microbial species. This may be the result of a variety of insults to the gastrointestinal tract including improper diet, antibiotics, and pathogen ingestion. Antibodies which adhere to the opportunistic microbial organisms may be produced as disclosed herein and mixed with a protective protein matrix. The mixture may be given orally, and the antibodies may adhere to and destroy the opportunistic microbes. When given in the proper titer, the composition may restore balance to the subject's gastrointestinal biome.

The strategy of producing cross-reactive antibodies may also be used to produce compositions to treat infections outside of the gastrointestinal tract. External infections or those within bodily orifices and tissues which may be accessed with minimally invasive procedures may be treated with cross-reactive antibody mixtures as disclosed herein. These infections may be those occurring in parts of the body including the ear, throat, skin, and urinary bladder. A protective protein matrix may be mixed with the antibodies to protect them from the environment to be treated. The cross-reactivity of the antibodies negates the need to identify the precise species of the infecting organism.

This treatment confers passive immunity to patients. The nature of the treatment makes the associated risk factors comparable to that of eating food from the source where the antibodies were harvested (e.g., risk factors would be similar to that of eating an egg and a glass of milk). This is an effective treatment with less toxicity than the currently available alternative medicines.

One important limitation of using natural food-based products is that preparations are limited to the results allowed by natural processes. The present composition and methods of its use allow for the selective addition of specific antibodies and general immune factors (formulations) that are significantly higher than physiological levels that can normally be achieved in nature. The present invention also allows for a weighting of various factors in a manner as to create greater specificity to targeted diseases, pathogens, or toxins.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention. The following examples are intended to illustrate but not limit the invention.

EXAMPLES

The following examples include the disclosed therapeutic which was prepared as follows. Chickens (Rhode Island Red) were housed, fed, and cared for according to standard protocol for commercial egg-laying hens. They were raised from hatchlings and fed a high protein diet comprising 20% or more protein for the first 10-15 weeks after hatching. Feed included 2.5-5.0 g calcium per day. Afterwards, the hens were fed a diet comprising less than 20% protein. Overall, the range of protein in the chicken feed was between 14-22 g per day. Adequate water was also provided.

The hens were vaccinated by subcutaneous injection with four commercially available animal vaccines. The first was ScourGuard 4KC available from Zoetis (Parsippany, New Jersey). This vaccine was a designed to prevent diarrhea caused by bovine rotavirus (serotypes G6 and G10), bovine coronavirus, enterotoxigenic strains of *Escherichia coli* having the K99 pili adherence factor, and *Clostridium perfringens* type C. The vaccine was provided as a liquid preparation of inactivated bovine rotavirus (serotypes G6 and G10) and coronavirus propagated on established cell lines, a K99 *E. coli* bacterin, and *C. perfringens* type C toxoid and included an adjuvant to enhance the immune response. The second vaccine *C. perfringens* Type A Toxoid supplied by Elanco (Greenfield, Indiana) and included *C. perfringens* Type A, enterotoxin and an adjuvant. This vaccine was designed to prevent disease caused by the alpha toxin (Type A) of *C. perfringens*. The third vaccine was *Campylobacter Fetus-Jejuni* Bacterin supplied by Colorado Serum (Denver, Colorado). This vaccine is an aqueous suspension of inactivated cultures (killed bacteria) of *Campylobacter fetus* and *Campylobacter jejuni*. It contained aluminum hydroxide as an adjuvant and thimerosal as a preservative. The fourth vaccine was Neopar supplied by NeoTech (Dresden, Tennessee). This vaccine was a modified live virus vaccine containing a high antigenic mass per dose of a highly immunogenic strain of canine parvovirus and included gentamicin and amphotericin B as preservatives. Consequently, the hens were vaccinated against the following diarrhea-causing organisms: coronavirus, *C. perfringens*, rotavirus, *Salmonella, E. coli, Campylobacter*, and parvovirus.

Following vaccinations, eggs were collected from the hens. A dehydrated egg powder was prepared from the whole shell eggs by drying the eggs as described herein and grinding the dehydrated product to produce an egg powder.

A sample of the egg powder was sent to an ISO/IEC 17025:2005 accredited commercial testing facility to assess the microbial and heavy metal contents. The laboratory report is provided as Table 1. These results indicate that the egg powder is safe for ingestion.

TABLE 1

Analysis of Egg Powder

| Analysis | Result | Per Unit | Specifications | Method |
|---|---|---|---|---|
| Mercury | <0.001 | ppm | Report | ICP-MS USP<730> |
| Lead | 0.117 | ppm | Report | ICP-MS USP<730> |
| Arsenic | 0.013 | ppm | Report | ICP-MS USP<730> |
| Cadmium | 0.006 | ppm | Report | ICP-MS USP<730> |
| Identification by FTIR | 97.48% positive | | Report | FTIR |
| Total Aerobic Microbial Count | <10 | CFU/g | Report | USP<2021> |
| *E. coli* | Absent | per 10 g | Absent | USP<2022> |
| *Salmonella* | Absent | per 10 g | Absent | USP<2022> |
| Coliforms | <3.0 | MPN/g | Report | AOAC 966.24 |
| *Staphylococcus aureus* | Absent | per 10 g | Absent | USP<2021> |
| Total Yeast and Mold | <10 | CFU/g | <100 CFU/g | USP<2021> |
| Yeast | <10 | CFU/g | <100 CFU/g | |
| Mold | <10 | CFU/g | <100 CFU/g | |

USP = microbial limits preparatory testing;
AOAC = Association of Official Agricultural Chemists
CFU = colony forming units;
ICP-MS = Inductively Coupled Plasma Mass Spectrometry;
FTIR = Fourier transform infrared spectroscopy The egg powder was combined in a ratio of 50:50 by weight with commercially available bovine colostrum powder which was derived from non-hyperimmune cattle. The mixture was stored at room temperature until reconstituted with water for use as described below. Each dose comprised 5 g of the mixture along with a vanilla flavoring for palatability.

Example 1—Treatment of Parvovirus in 6-Week Old Canine

Canine parvovirus is a highly contagious viral disease that can produce a life-threatening illness. The virus attacks rapidly dividing cells in a dog's body, most severely affecting the intestinal tract. Parvovirus also attacks the white blood cells, and when young animals are infected, the virus can damage the heart muscle and cause lifelong cardiac problems.

There are no drugs or treatments generally available that can kill parvovirus. Standard of care treatment consists of aggressive supportive care to control symptoms. Dogs infected with parvovirus need intensive treatment in a veterinary hospital, where they receive antibiotics (which has no effect on the parvovirus), drugs to control the vomiting, intravenous fluids and other supportive therapies. This entails considerable expense; the average hospital stay is 5 to 7 days at a cost of several thousand dollars. Even with medical support canine parvovirus mortality rates range from 5%-20%. Without treatment, the mortality rate is 90%.

A six-week-old puppy (canine) was stricken with severe diarrhea and taken to a veterinary hospital for diagnosis and treatment. The attending veterinarian diagnosed the patient with parvovirus, which was confirmed with an ELISA fecal test.

With the pet owner's permission, in addition to standard of care treatment, the attending veterinarian administered an antibody treatment consisting of hyperimmunized egg powder (raised in vaccinated chickens as described herein) containing parvovirus antibodies mixed with whole colostrum powder. The formulation was mixed with a small quantity of water and administered orally to the patient, who was taken home by the owner. The next morning the patient was reexamined at the hospital by the veterinarian. The puppy was symptom free, with normal temperature, solid stool, and no evidence of physical distress. A fecal ELISA test confirmed the absence of parvovirus infection. The antibody/colostrum formulation effectively conferred passive immunity to the patient and eradicated the parvovirus infection and sequelae within 24 hours of treatment.

Example 2—Treatment of Parvovirus in Study Group of 10 Canines

Objective

The objective of this study was to evaluate the tolerability and efficacy of the disclosed treatment in parvovirus induced diarrhea episodes for dogs residing in the United States.

Methods

The study was an open-label, multi-center, study of canine patients between one month and five years of age. The selection and recruitment of patients for the trial was conducted by the supervising veterinarian or health provider. Additional clinical or animal shelter personnel assisted in subject care and logistics as necessary. Pet owner informed consent was obtained upon enrollment.

Study Group:

All participating subjects presented with a "moderate" to "severe" diarrhea profile, as reported by the attending veterinarian. Laboratory diagnostic tests were performed to confirm that parvovirus was the causative agent or etiology of the canine diarrhea.

The study group consisted of ten parvovirus positive subjects, with all ten completing the study. All study subjects were observed, and data was collected, over 24 hours.

There was no negative control group treated with the standard of care regimen of antibiotics and dehydration. Antibiotic and active hydration treatment was withheld for all subjects pending subject status review the following day.

The treatment was as disclosed herein and included hyperimmunized egg powder created from eggs laid by hens which had been immunized as described herein and whole colostrum powder created from bovine colostrum. The animals which provided the colostrum were not vaccinated with parvovirus vaccine. The treatment was packaged in single dose sachets containing 5 g of powder. The treatment was administered orally, with the contents of one sachet resuspended in approximately 2 oz. of standard drinking water. Test subjects were required to drink the entire suspension in one sitting, immediately after preparation was complete. Subjects remained under on-site observation for 10 minutes after administration.

Reported parameters as measured for each subject include stool frequency, stool consistency, and doctor reported well-being. These three criteria were found to be the most significant to both the attending veterinarians and the subject's owner in assessing the state and the improvement of the subject's condition.

Results

Subjects were evaluated against standard of care states: sever, bloody diarrhea; lethargy; anorexia; fever; vomiting; and severe weight loss.

All subjects were rated as moderate to severely ill, up to and including states such as listless and minimally responsive.

Dramatic improvements were observed in all subjects within 12 hours of initial administration of the disclosed therapy. Stool frequency and consistency returned to normal. Vomiting and bloody stool were eliminated. Normal activity resumed and no adverse side effects were observed.

In contrast, standard of care subjects (not included in this study) typically rank severely ill at 24 hours and seriously ill after 48 hours.

One test subject suffering declining well-being was treated with the disclosed therapy after undergoing several days of standard of care treatment. Although diarrhea-related symptoms subsided, the subject subsequently died from systemic failure resulting from the initial parvovirus infection.

CONCLUSION

This study provides evidence that the disclosed treatment is highly effective in managing acute parvovirus diarrhea in canine patients with significant reductions in both the duration and severity of illness. It is also effective in the dietary management of acute parvovirus diarrhea, greatly reducing the length and severity of illness. The treatment is a safe, non-antibiotic dietary intervention that was well tolerated by the test subjects.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

I claim:

1. A composition for treatment or prevention of diarrhea or enteric infection in animals, the composition comprising:
    a. a mixture of IgY antibodies specific for a plurality of antigens obtained from a plurality of organisms, wherein the organisms cause diarrhea in animals, and wherein a mercury content in the mixture is less than 0.001 ppm; and
    b. a protective matrix comprising protein, wherein the protein is derived from a non-hyperimmune animal source and comprises at least 20 percent of the composition by weight.

2. The composition of claim 1, wherein the mixture of IgY antibodies is obtained from one or more eggs laid by one or more birds, wherein each of the one or more birds have been vaccinated with the plurality of antigens.

3. The composition of claim 1, wherein each of the plurality of organisms is independently selected from the group consisting of: a species of the genus *Clostridium*, a species of the genus *Yersinia*, a species of the genus *Brachyspira*, a species of the genus *Campylobacter*, *Escherichia coli*, *Helicobacter* spp., a species of the genus *Salmonella*, a species of the genus *Leptospira*, *Providencia alcalifaciens*, *Mycobacterium paratuberculosis*, *Lawsonia intracellularis*, bovine viral diarrhea virus, infectious bovine rhinotracheitis virus, coronavirus, rotavirus, parvovirus, paramyxovirus, hepatitis virus, feline leukemia virus, feline immunodeficiency virus, feline panleukopenia virus, astrovirus, transmissible gastroenteritis, *Giardia*, *Coccidia*, *Entamoeba histolytica*, *Cryptosporidium*, roundworm, whipworm, spirochetes, yeasts, or molds.

4. The composition of claim 1 wherein each of the plurality of organisms is independently selected from group consisting of: rotavirus, coronavirus, *Escherichia coli*, *Clostridium perfringens*, *Campylobacter fetus*, *Campylobacter jejuni*, or parvovirus.

5. The composition of claim 1, wherein the animal is a member of the Canidae or Felidae families.

6. The composition of claim 1, wherein the non-hyperimmune animal is a ruminant.

7. The composition of claim 1, wherein the animal is bovine.

8. A method comprising:
    a. providing a mixture of IgY antibodies specific for a plurality of antigens obtained from a plurality of organisms, wherein the organisms cause diarrhea in animals, wherein a mercury content in the mixture is less than 0.001 ppm and wherein one of the organisms is parvovirus;
    b. combining the mixture of IgY antibodies with a protective matrix comprising protein, wherein the combining results in a composition, and wherein the protein is derived from a non-hyperimmune animal source and comprises at least 20 percent of the composition by weight; and
    c. treating a sick animal using the composition, the treatment comprising:
        administering the composition to a sick animal infected with at least one of the organisms;
        monitoring one or more symptoms of the sickness; and establishing an efficacy of the composition based on an absence of the symptoms and an eradication of the sickness in the animal based on testing.

9. The method of claim 8, wherein the mixture of IgY antibodies is obtained from one or more eggs laid by one or more birds, wherein each of the one or more birds have been vaccinated with the plurality of antigens.

10. The method of claim 8, wherein each of the plurality of organisms is independently selected from the group consisting of: a species of the genus *Clostridium*, a species of the genus *Yersinia*, a species of the genus *Brachyspira*, a species of the genus *Campylobacter, Escherichia coli, Helicobacter* spp., a species of the genus *Salmonella*, a species of the genus *Leptospira, Providencia alcalifaciens, Mycobacterium paratuberculosis, Lawsonia intracellularis*, bovine viral diarrhea virus, infectious bovine rhinotracheitis virus, coronavirus, rotavirus, parvovirus, paramyxovirus, hepatitis virus, feline leukemia virus, feline immunodeficiency virus, feline panleukopenia virus, astrovirus, transmissible gastroenteritis, *Giardia, Coccidia, Entamoeba histolytica, Cryptosporidium*, roundworm, whipworm, spirochetes, yeasts, or molds.

11. The method of claim 8 wherein each of the plurality of organisms is independently selected from group consisting of: rotavirus, coronavirus, *Escherichia coli, Clostridium perfringens, Campylobacter fetus, Campylobacter jejuni*, or parvovirus.

12. The method of claim 8, wherein the animal is a member of the Canidae or Felidae families.

13. The method of claim 8, wherein the non-hyperimmune animal is a ruminant.

14. The method of claim 8, wherein the animal is bovine.

15. The composition of claim 1, wherein the composition is administered as a vaccine to a healthy animal to provide immunity against illness caused by at least one of the organisms or as a treatment to a sick animal infected with at least one of the organisms.

16. The method of claim 8, further comprising administering the composition as a vaccine to a healthy animal to provide immunity against illness caused by at least one of the organisms.

17. A composition comprising:
   a. a mixture of IgY antibodies specific for a plurality of antigens obtained from a plurality of organisms, wherein the organisms cause diarrhea in animals, and wherein a mercury content in the mixture is less than 0.001 ppm; and
   b. a protective matrix comprising protein, wherein the protein is derived from a non-hyperimmune animal source and comprises at least 20 percent of the composition by weight, wherein the composition is administered to a healthy animal on a daily basis as a prophylactic against illness caused by at least one of the organisms.

18. A method for preparing a treatment or preventative composition for diarrhea or enteric infection in animals, the method comprising:
   a. providing a mixture of IgY antibodies specific for a plurality of antigens obtained from a plurality of organisms, wherein the organisms cause diarrhea in animals, wherein one of the organisms is parvovirus, and wherein a mercury content in the mixture is less than 0.001 ppm; and
   b. combining the mixture of IgY antibodies with a protective matrix comprising protein, wherein the protein is derived from a non-hyperimmune animal source and comprises at least 20 percent of the composition by weight.

* * * * *